United States Patent
Lim et al.

(10) Patent No.: US 12,205,046 B2
(45) Date of Patent: Jan. 21, 2025

(54) DEVICE FOR ENSEMBLING DATA RECEIVED FROM PREDICTION DEVICES AND OPERATING METHOD THEREOF

(71) Applicant: ELECTRONICS AND TELECOMMUNICATIONS RESEARCH INSTITUTE, Daejeon (KR)

(72) Inventors: Myung-eun Lim, Daejeon (KR); Do Hyeun Kim, Goyang (KR); Jae Hun Choi, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 1026 days.

(21) Appl. No.: 17/115,373

(22) Filed: Dec. 8, 2020

(65) Prior Publication Data
US 2021/0174229 A1  Jun. 10, 2021

(30) Foreign Application Priority Data
Dec. 10, 2019 (KR) .................. 10-2019-0164113

(51) Int. Cl.
*G06N 5/04* (2023.01)
*G06F 18/2113* (2023.01)
(Continued)

(52) U.S. Cl.
CPC ........... *G06N 5/04* (2013.01); *G06F 18/2113* (2023.01); *G06F 18/213* (2023.01); *G06N 3/084* (2013.01); *G06N 20/20* (2019.01)

(58) Field of Classification Search
None
See application file for complete search history.

(56) References Cited

U.S. PATENT DOCUMENTS

2014/0343955 A1  11/2014  Raman
2016/0358099 A1  12/2016  Sturlaugson et al.
(Continued)

FOREIGN PATENT DOCUMENTS

KR  1020090053578 A  5/2009
KR  1020160143512 A  12/2016
(Continued)

OTHER PUBLICATIONS

Robinzonov et al., "Boosting Techniques for Nonlinear Time Series Models," 2010, https://epub.ub.uni-muenchen.de/11330/1/tr075.pdf.*
(Continued)

*Primary Examiner* — Ryan Barrett

(57) ABSTRACT

Disclosed is a device which includes a data manager, a learner, and a predictor. The data manager generates output data based on time-series data, receives device prediction results corresponding to the output data from the prediction devices, and calculates device errors based on the difference between device prediction results and time-series data. The learner may adjust a parameter group of a prediction model for generating device weights, based on device prediction results and device errors. The predictor generates the ensemble result of first and second device prediction results based on device weights.

19 Claims, 12 Drawing Sheets

(51) Int. Cl.
  *G06F 18/213* (2023.01)
  *G06N 3/084* (2023.01)
  *G06N 20/20* (2019.01)

(56) References Cited

U.S. PATENT DOCUMENTS

| | | | |
|---|---|---|---|
| 2017/0147777 | A1 | 5/2017 | Kim et al. |
| 2017/0357760 | A1 | 12/2017 | Han et al. |
| 2018/0137427 | A1* | 5/2018 | Hsieh ................. G06N 20/20 |
| 2019/0303197 | A1* | 10/2019 | Li ..................... G06F 9/4887 |
| 2020/0151610 | A1* | 5/2020 | Chueh ................ G06N 20/20 |
| 2020/0184284 | A1* | 6/2020 | Lim .................... G06N 3/045 |
| 2020/0293887 | A1* | 9/2020 | De Brouwer ......... G06N 3/084 |
| 2022/0198302 | A1* | 6/2022 | Nishimura ............ G08G 1/005 |
| 2022/0254513 | A1* | 8/2022 | Chen ................... G06N 20/20 |

FOREIGN PATENT DOCUMENTS

| | | |
|---|---|---|
| KR | 10-2017-0140757 A | 12/2017 |
| KR | 10-2018-0061553 A | 6/2018 |
| KR | 10-2018-0099193 A | 9/2018 |
| KR | 10-2019-0086345 A | 7/2019 |
| KR | 10-2019-0092217 A | 8/2019 |

OTHER PUBLICATIONS

Yang et al., "Federated Machine Learning: Concept and Applications," Jan. 2019, ACM Trans. Intell. Syst. Technol., vol. 10, No. 2, Article 12, https://dl.acm.org/doi/10.1145/3298981.*
Junsawang et al., "Streaming chunk incremental learning for class-wise data stream classification with fast learning speed and low structural complexity," Sep. 9, 2019, https://www.ncbi.nlm.nih.gov/pmc/articles/PMC6733468/.*

* cited by examiner

DEVICE FOR ENSEMBLING DATA RECEIVED FROM PREDICTION DEVICES AND OPERATING METHOD THEREOF

CROSS-REFERENCE TO RELATED APPLICATIONS

This application claims priority under 35 U.S.C. § 119 to Korean Patent Application No. 10-2019-0164113 filed on Dec. 10, 2019, in the Korean Intellectual Property Office, the disclosures of which are incorporated by reference herein in their entireties.

BACKGROUND

Embodiments of the present disclosure described herein relate to processing of data, and more particularly, relate to a device which ensembles data received from prediction devices and an operating method thereof.

There is a need to predict a future health state beyond curing the current disease to lead a healthy life. To predict the future health state, there is an increasing demand for diagnosing diseases by analyzing big data or predicting future disease risk. The development of industrial technology and information and communication technology supports the building of big data. Moreover, technologies such as artificial intelligence that learns electronic devices such as computers to provide various services by using such the big data are emerging. In particular, to predict the future health state, a method of building a learning model using a variety of medical data or health data has been proposed.

It is possible to make better accurate predictions as the size of the data is larger. However, due to various causes such as ethical issues, legal issues, and personal privacy issues, it may be difficult to share data between various medical institutions. For this reason, it is actually difficult to build big data, using the integrated medical data. A method of learning individual prediction models by using data individually built in various medical institutions, and utilizing prediction results to predict the future health state of a patient may be sought as the solution to the problems peculiar to such the medical data.

SUMMARY

Embodiments of the present disclosure provide a device which ensembles data received from a plurality of prediction devices such that reliability, accuracy, and efficiency of future health state prediction are secured, and an operating method thereof.

According to one embodiment, a device which ensembles data received from a plurality of prediction devices includes a data manager and a learner. The data manager generates output data based on time-series data, provides the output data to a first prediction device and a second prediction device, receives a first device prediction result corresponding to the output data from the first prediction device, receives a second device prediction result corresponding to the output data from the second prediction device, calculates a first device error based on a difference between the first device prediction result and the time-series data, and calculates a second device error based on a difference between the second device prediction result and the time-series data. The learner adjusts a parameter group of a prediction model for generating a first device weight corresponding to the first prediction device and a second device weight corresponding to the second prediction device, based on the first device prediction result, the second device prediction result, the first device error, and the second device error. The output data includes first cumulative data including features before a first time in the time-series data, and second cumulative data including features before a second time in the time-series data.

For example, the first prediction device may generate first prediction features corresponding to the second time based on the first cumulative data, generate second prediction features corresponding to a third time after the second time based on the second cumulative data, and generate the first device prediction result including the first prediction features and the second prediction features. The second prediction device may generate third prediction features corresponding to the second time based on the first cumulative data, generate fourth prediction features corresponding to the third time after the second time based on the second cumulative data, and generate the second device prediction result including the third prediction features and the fourth prediction features.

For example, the learner may extract prediction features during a window time interval before a target time from the first device prediction result to generate a first feature window, extract prediction features during the window time interval before the target time from the second device prediction result to generate a second feature window, extract prediction features during the window time interval before the target time from the first device error to generate a first error window, extract prediction features during the window time interval before the target time from the second device error to generate a second error window, and adjust the parameter group based on the first feature window, the second feature window, the first error window, and the second error window.

For example, the learner may generate the first and second feature windows and the first and second error windows by making zero-padding on values for a time before the target time when the target time is a first time of the first and second device prediction results and the first and second device errors.

For example, the learner may analyze a trend of the window time interval for the first feature window to generate a first prediction result trend, analyze a trend of the window time interval for the second feature window to generate a second prediction result trend, analyze a trend of the window time interval for the first error window to generate a first error trend, analyze a trend of the window time interval for the second error window to generate a second error trend, and adjust the parameter group based on the first prediction result trend, the second prediction result trend, the first error trend, and the second error trend.

For example, the learner may extract a prediction feature vector corresponding to a prediction time based on the first and second prediction result trends and the first and second device prediction results, and extract a prediction error vector corresponding to the prediction time based on the first and second error trends and the first and second device errors. For example, the learner may generate the first device weight and the second device weight, based on the prediction feature vector and the prediction error vector. Each of the first device weight and the second device weight may include weight values corresponding to each of a plurality of items.

For example, the learner may generate the first device weight and the second device weight based on the first device prediction result, the second device prediction result, the first device error, and the second device error, generate a reference device weight based on the first device prediction result and the second device prediction result, and compare the reference device weight with the first and second device weights to adjust the parameter group. For example, the learner may calculate a first difference between a prediction feature of the first device prediction result corresponding to a prediction time and an actually-measured value corresponding to the prediction time, calculate a second difference between a prediction feature of the second device prediction result corresponding to the prediction time and the actually-measured value, and generate the reference device weight based on the first difference and the second difference.

According to one embodiment, a device which ensembles data received from a plurality of prediction devices includes a data manager and a predictor. The data manager provides output data to a first prediction device and a second prediction device, receives a first device prediction result corresponding to the output data from the first prediction device, and receives a second device prediction result corresponding to the output data from the second prediction device. The predictor generates a prediction feature vector corresponding to a prediction time, based on the first device prediction result, the second device prediction result, a first trend of the first device prediction result during a window time interval, and a second trend of the second device prediction result during the window time interval, generates a first device weight and a second device weight of each of a plurality of items, based on the prediction feature vector, and generates an ensemble result of the first and second device prediction results corresponding to the prediction time, based on the first device weight and the second device weight.

For example, the data manager may generate the output data including first cumulative data including features before a first time in time-series data, and second cumulative data including features before a second time in the time-series data.

For example, the data manager may generate the output data based on time-series data, calculate a first device error based on a difference between the first device prediction result and the time-series data, and calculate a second device error based on a difference between the second device prediction result and the time-series data. The predictor may generate a prediction error vector corresponding to the prediction time, based on the first device error, the second device error, a third trend of the first device error during the window time interval, and a fourth trend of the second device prediction result during the window time interval, and generate the first device weight and the second device weight further based on the prediction error vector.

For example, the predictor may extract prediction features during the window time interval before a target time from the first device prediction result to generate a first feature window, extract prediction features during the window time interval before the target time from the second device prediction result to generate a second feature window, generate the first trend based on the first feature window, and generate the second trend based on the second feature window. For example, the predictor may generate the first and second feature windows by making zero-padding on values a time before the target time when the target time is a first time of the first and second device prediction results.

For example, the predictor may generate the prediction feature vector based on a feature vector generated by the first and second trends corresponding to a time before the prediction time, the first and second trends corresponding to the prediction time, and the first and second device prediction results corresponding to the prediction time.

For example, the predictor may apply the first device weight to the first device prediction result corresponding to the prediction time to generate a first result, apply the second device weight to the second device prediction result corresponding to the prediction time to generate a second result, and generate the ensemble result based on the first result and the second result.

According to one embodiment, an operating method of a device which ensembles data received from a plurality of prediction devices includes generating output data including first cumulative data including features before a first time in time-series data and second cumulative data including features before a second time in the time-series data, transmitting the output data together with a prediction request to a first prediction device and a second prediction device, receiving a first device prediction result obtaining by responding to the prediction request, from the first prediction device, receiving a second device prediction result obtaining by responding to the prediction request, from the second prediction device, calculating a first device error based on a difference between the first device prediction result and the time-series data, calculating a second device error based on a difference between the second device prediction result and the time-series data, and generating a first device weight corresponding to the first prediction device and a second device weight corresponding to the second prediction device, based on the first device prediction result, the second device prediction result, the first device error, and the second device error.

For example, the generating of the first device weight and the second device weight may include analyzing the first device prediction result during a window time interval to generate a first prediction result trend, analyzing the second device prediction result during the window time interval to generate a second prediction result trend, analyzing the first device error during the window time interval to generate a first error trend, analyzing the second device error during the window time interval to generate a second error trend, generating a feature vector corresponding to a prediction time based on the first and second prediction result trends and the first and second device prediction results, generating an error vector corresponding to the prediction time based on the first and second error trends and the first and second device errors, and generating the first and second device weights based on the feature vector and the error vector.

For example, the method may further include comparing a reference device weight with the first device weight and the second device weight to adjust a parameter of a prediction model.

For example, the method may further include applying the first device prediction result corresponding to a prediction time to the first device weight to generate a first result, applying the second device prediction result corresponding to the prediction time to the second device weight to generate a second result, and generating an ensemble result based on the first result and the second result.

BRIEF DESCRIPTION OF THE FIGURES

The above and other objects and features of the present disclosure will become apparent by describing in detail embodiments thereof with reference to the accompanying drawings.

DETAILED DESCRIPTION

Hereinafter, embodiments of the present disclosure will be described clearly and in detail with reference to accompanying drawings to such an extent that an ordinary one in the art implements embodiments of the present disclosure.

Figure 1:
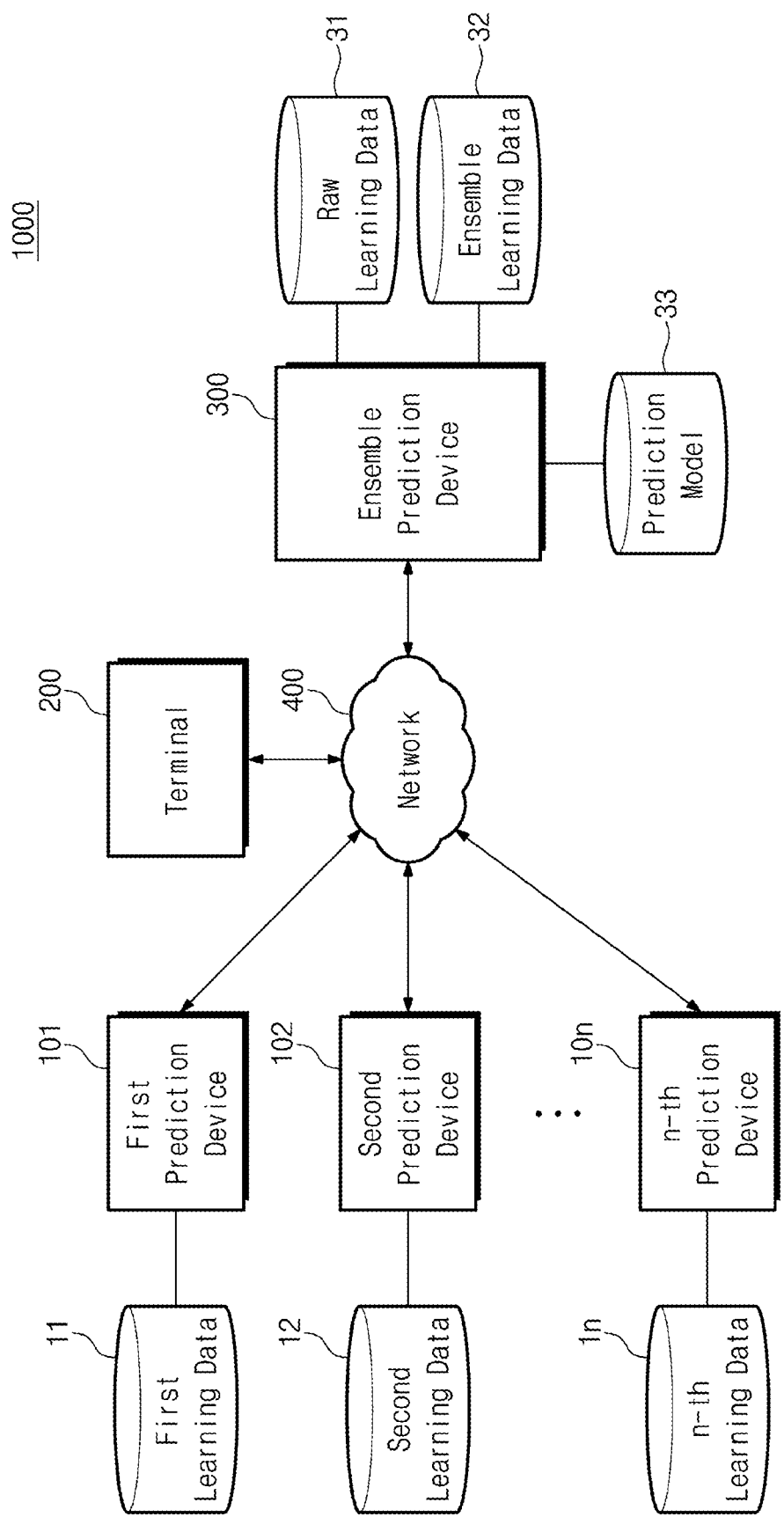
FIG. 1 is a diagram illustrating a health state prediction system according to an embodiment of the present disclosure.

FIG. 1 is a diagram illustrating a health state prediction system according to an embodiment of the present disclosure. Referring to FIG. 1, a health state prediction system 1000 includes first to n-th prediction devices 101 to 10$n$, a terminal 200, an ensemble prediction device 300, and a network 400. For convenience of description, it is illustrated that the number of prediction devices 101 to 10$n$ is 'n', but the number of health prediction devices is not limited thereto.

Each of the first to n-th prediction devices 101 to 10$n$ may predict a user's health state based on the individually built prediction model. Herein, the prediction model may be a structure modeled to predict a health state at a future point, using time-series medical data. Each of the first to n-th prediction devices 101 to 10$n$ may generate and learn the prediction model, using first to n-th learning data 11 to 1$n$.

Each of the first to n-th prediction devices 101 to 10$n$ may be provided to different medical institutions or different public institutions. The first to n-th learning data 11 to 1$n$ may be individually stored in a database to generate and learn the prediction model of each of the institutions. The different medical institutions or the different public institutions may individually learn the prediction model, may apply the user's time-series medical data to the prediction model built depending on this learning, and may predict the health state of the user in the future.

Each of the first to n-th prediction devices 101 to 10$n$ may receive output data, which is generated based on raw learning data 31, from the ensemble prediction device 300 through the network 400. Herein, the raw learning data 31 may include time-series medical data for learning a prediction model 33 built in the ensemble prediction device 300. The time-series medical data may include features corresponding to each of a plurality of times. It may be understood that the output data is data obtained by accumulating features of previous times of each of the plurality of times. The details of the output data will be described later.

The first to n-th prediction devices 101 to 10$n$ may generate first to n-th device prediction results by applying output data to each built prediction model respectively. Here, it may be understood that the first to n-th device prediction results are the result of predicting the health state at a prediction time based on the output data. The first to n-th device prediction results may be provided to the ensemble prediction device 300 through the network 400.

Because the first to n-th device prediction results are generated based on different prediction models, the first to n-th device prediction results may have different data values. The reason is that each of the first to n-th prediction devices 101 to 10$n$ learns and builds the prediction model based on different time-series medical data, that is, the different first to n-th learning data 11 to 1$n$. Due to the sensitive characteristics of medical data, such as ethical issues, legal issues, and personal privacy issues, it is difficult to share data for each medical institution, and it is difficult to build big data. Accordingly, the first to n-th prediction devices 101 to 10$n$ may individually build a prediction model. The ensemble prediction device 300 may ensemble the prediction results of the raw learning data 31 from the first to n-th prediction devices 101 to 10$n$, and thus it may be possible to predict future health in consideration with a variety of data learning.

The first to n-th prediction devices 101 to 10$n$ analyze time-series data TD based on different prediction models. Medical institutions or hospitals learn prediction models from an internally-built database, in an environment where data sharing and exchange is difficult due to the sensitivity of medical data. Due to the characteristics of the medical environment, time-series medical data may be biased to a specific medical institution. Specialized hospitals for specific diseases may collect medical data concentrated on the specific diseases. Furthermore, the range of time-series medical data may be biased to a specific medical institution, due to the deviation of the health state of a visiting patient group. In such the situation, the health state prediction system 1000 according to an embodiment of the present disclosure may have the same effect as collaboration by generating results using prediction models built in different manners to ensemble the results.

The terminal 200 may provide a request signal for predicting the future health of the patient(s) or for learning the prediction model 33. The terminal 200 may be an electronic device capable of providing a request signal, such as a smartphone, a desktop, a laptop, a wearable device, or the like. For example, the terminal 200 may provide a request signal to the ensemble prediction device 300 through the network 400. In this case, the prediction model 33 of the ensemble prediction device 300 may be learned. Alternatively, the first to n-th prediction devices 101 to 10$n$ and the ensemble prediction device 300 may diagnose the health state of a user or may predict the future health state of the user.

The ensemble prediction device 300 learns the prediction model 33 using the first to n-th device prediction results. Here, as described above, the prediction model 33 may be a structure modeled to finally predict future health states by ensembling device prediction results in which health states predicted by each of the first to n-th prediction devices 101 to 10$n$. The ensemble prediction device 300 may transmit, to the first to n-th prediction devices 101 to 10$n$, output data, which is generated based on the raw learning data 31, together with a prediction request. The ensemble prediction device 300 may receive the first to n-th device prediction results from the first to n-th prediction devices 101 to 10n. The ensemble prediction device 300 may generate first to n-th device errors by calculating the difference between time-series medical data and the first to n-th device prediction results. The ensemble prediction device 300 may generate ensemble learning data 32 including the first to n-th device prediction results and the first to n-th device errors. The ensemble prediction device 300 learns the prediction model 33 based on the ensemble learning data 32.

The raw learning data 31 may include time-series medical data indicating the health state of the user generated by diagnosis, treatment, examination, medication prescription, or the like. For example, the time-series medical data may be Electronic Medical Record (EMR) data or Personal Health Record (PHR) data. The raw learning data 31 may include time-series medical data collected by an institution in which the ensemble prediction device 300 is implemented. The raw learning data 31 may be integrally managed by the ensemble prediction device 300. The raw learning data 31 may be stored as a database in the server or storage medium of the ensemble prediction device 300.

The ensemble learning data 32 may include the first to n-th device prediction results and the first to n-th device errors. The ensemble learning data 32 may be integrally managed by the ensemble prediction device 300. The ensemble learning data 32 may be stored as a database in the server or storage medium of the ensemble prediction device 300.

It may be understood that the prediction model 33 is an ensemble model for ensembling the first to n-th device prediction results. The ensemble model may be a structure for processing the first to n-th device prediction results so as to have the same dimensions as the first to n-th device prediction results, without simply merging the prediction results. The prediction model 33 may be managed as a weight group (parameter group) such that an artificial neural network for such the processing is implemented. The parameter group may be stored as a database in the server or storage medium of the ensemble prediction device 300. Moreover, the detailed content in which the ensemble prediction device 300 learns the prediction model 33 and generates the ensemble result using the learned prediction model 33 will be described later.

The network 400 may be configured to perform data communication between the first to n-th prediction devices 101 to 10n, the terminal 200, and the ensemble prediction device 300. The first to n-th prediction devices 101 to 10n, the terminal 200, and the ensemble prediction device 300 may exchange data through the network 400 by wire or wirelessly.

Figure 2:
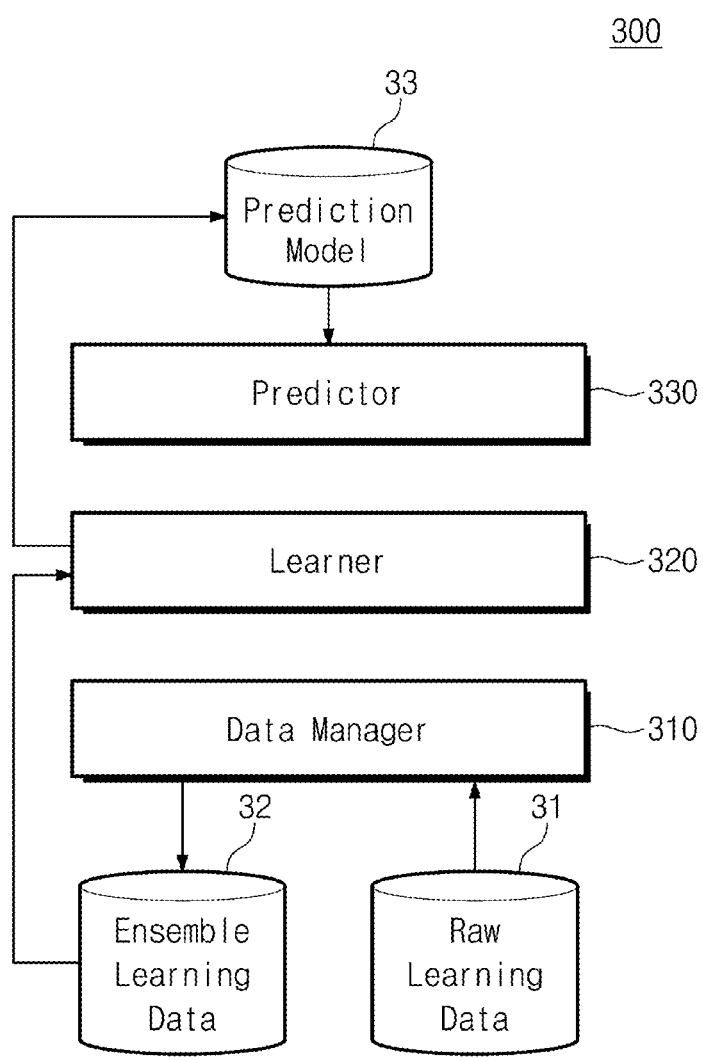
FIG. 2 is a block diagram of the ensemble prediction device of FIG. 1.

FIG. 2 is a block diagram of the ensemble prediction device of FIG. 1. It may be understood that the ensemble prediction device 300 of FIG. 2 is a configuration for learning the prediction model 33 for generating an ensemble result, or for generating the ensemble result, by analyzing the prediction results for each device received from the first to n-th prediction devices 101 to 10n of FIG. 1. Referring to FIG. 2, the ensemble prediction device 300 includes a data manager 310, a learner 320, and a predictor 330.

The data manager 310, the learner 320, and the predictor 330 may be implemented in hardware, firmware, software, or the combination thereof. For example, the software (or firmware) may be executed by a processor (not illustrated) after being loaded onto a memory (not illustrated) included in the ensemble prediction device 300. For example, the data manager 310, the learner 320, and the predictor 330 may be implemented with hardware such as dedicated logic circuits such as Field Programmable Gate Array (FPGA) or Application Specific Integrated Circuit (ASIC).

The data manager 310 may manage the raw learning data 31 and the ensemble learning data 32. To learn the prediction model 33, the data manager 310 may generate output data using time-series data included in the raw learning data 31. It may be understood that the output data is data obtained by accumulating features of previous times based on each of a plurality of times in the time-series data. The data manager 310 may output the output data together with a prediction request to the first to n-th prediction devices 101 to 10n of FIG. 1. In this case, the first to n-th prediction devices 101 to 10n may generate first to n-th device prediction results for the output data, in response to the prediction request.

The data manager 310 may receive the first to n-th device prediction results from the first to n-th prediction devices 101 to 10n, respectively. The data manager 310 may calculate first to n-th device errors based on the difference between the time-series data and the first to n-th device prediction results. The first to n-th device prediction results and the first to n-th device errors may be merged and managed into the ensemble learning data 32. Herein, it may be understood that the merging is achieved by grouping the results by adding identification information about a prediction device, without modifying the first to n-th prediction results, that is, unique information.

The learner 320 may learn the prediction model 33, based on the ensemble learning data 32. The prediction model 33 may include an analysis model for calculating an ensemble result, which is the prediction result for a prediction time, by analyzing prediction results and errors for each device. The prediction model 33 may be built through artificial neural network or deep learning machine learning.

The learner 320 may generate and adjust the parameter group of the prediction model 33 by analyzing the ensemble learning data 32. The parameter group may be a set of all parameters included in the artificial neural network structure or the neural network of the prediction model 33. The learner 320 may generate the ensemble result by analyzing the ensemble learning data 32. The learner 320 may adjust the parameter group of the prediction model 33 such that the generated ensemble result has the expected comparison result (or such that the generated ensemble result is within a reference error from the comparison result). The comparison result may be an actual measurement value of the prediction time, and may be preset for the ensemble prediction device 300. The adjusted parameter group may be reflected to the prediction model 33 to be managed by the ensemble prediction device 300.

The predictor 330 may analyze device prediction results corresponding to a specific user and may generate the ensemble result, based on the prediction model 33 and the parameter group, which are learned from the learner 320. The data manager 310 may provide the first to n-th prediction devices 101 to 10n with output data of a specific user together with the prediction request. The first to n-th prediction devices 101 to 10n may generate the first to n-th device prediction results in response to the prediction request. The predictor 330 may analyze the first to n-th device prediction results and errors thereof, using the prediction model 33. Also, the ensemble result may be provided to the terminal 200 of FIG. 1, or the like.

Figure 3:
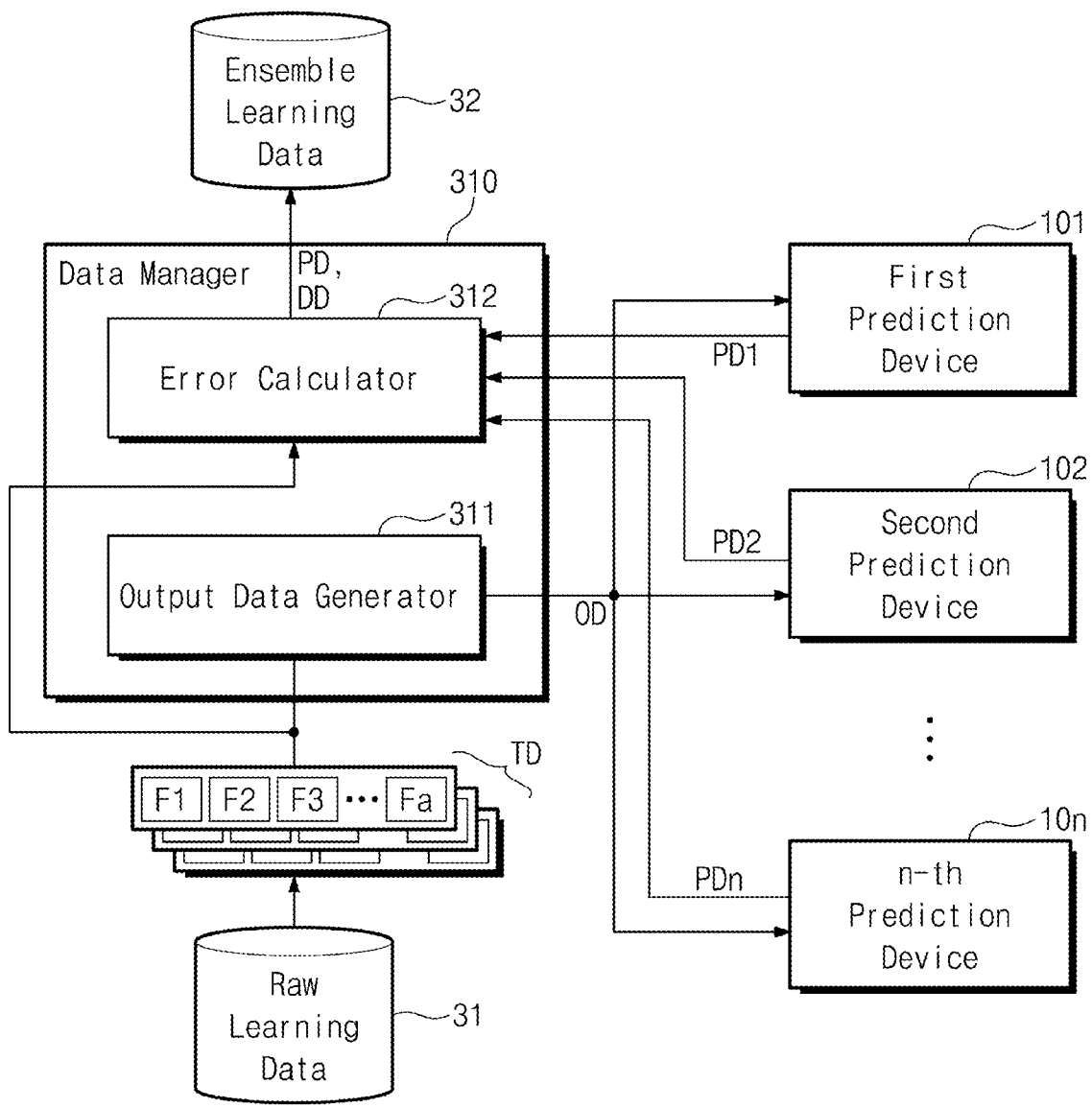
FIG. 3 is a diagram for describing an operation of the data manager of FIG. 2.

FIG. 3 is a diagram for describing an operation of the data manager of FIG. 2. Referring to FIG. 3, the data manager 310 includes an output data generator 311 and an error calculator 312. The data manager 310 receives time-series data TD. In an operation of learning the prediction model 33, the time-series data TD may be at least part of the raw learning data 31 managed by a server (not illustrated) or a storage (not illustrated). In an operation of predicting the future state using the learned prediction model 33, the time-series data TD may be provided from the terminal 200 of FIG. 1 or may be generated or collected by the ensemble prediction device 300.

The time-series data TD may be a set of data, which is recorded as time goes on and has a temporal order. The time-series data TD may include at least one or more features F1 to Fa corresponding to each of a plurality of times arranged in a time-series manner. For example, the time-series data TD may include time-series medical data indicating the health state of a user generated by diagnosis, treatment, medication prescription, or the like in medical institutions, such as an electronic medical record (EMR). The features F1 to Fa may refer to values corresponding to each of the items diagnosed, tested, or prescribed. For example, the item may indicate various health indicators such as blood pressure, blood sugar, cholesterol level, weight, or the like. For clarity of descriptions, the time-series medical data is exemplified, but the type of the time-series data TD is not limited thereto. The time-series data TD may be generated and collected in various fields such as entertainment, retail, smart management, and the like.

The output data generator 311 may generate output data OD based on the time-series data TD. The output data OD may include accumulated data obtained by extracting the features F1 to Fa of times before each of the plurality of times. For example, the output data generator 311 may include the first cumulative data including features F1 to Fa of times before the first time, and may generate second cumulative data including features F1 to Fa of times before the second time after the first time. The detailed process of generating output data OD will be described later with reference to FIG. 4.

The data manager 310 may provide the first to n-th prediction devices 101 to 10n with the output data OD together with the prediction request. The first to n-th prediction devices 101 to 10n may analyze the output data OD in response to the prediction request, using the prediction model built individually. As the analysis result, the first to n-th prediction devices 101 to 10n may generate the first to n-th device prediction results PD1 to PDn, respectively. The first to n-th device prediction results PD1 to PDn (PD) may indicate a health state for a future point based on cumulative data.

The error calculator 312 may receive the first to n-th device prediction results PD and may generate the first to n-th device errors DD. The error calculator 312 may calculate the difference between the time-series data TD and the first to n-th device prediction results PD. The error calculator 312 may calculate the difference between features F1 to Fa for each of the plurality of times and the prediction features of the first to n-th device prediction results PD to generate the first to n-th device errors DD. The first to n-th device prediction results PD and the first to n-th device errors DD may be included in the ensemble learning data 32 and may be provided to the learner 320 of FIG. 2. In an operation of predicting the future state using the learned prediction model 33, the first to n-th device prediction results PD and the first to n-th device errors DD may be provided to the predictor 330 of FIG. 2.

Figure 4:
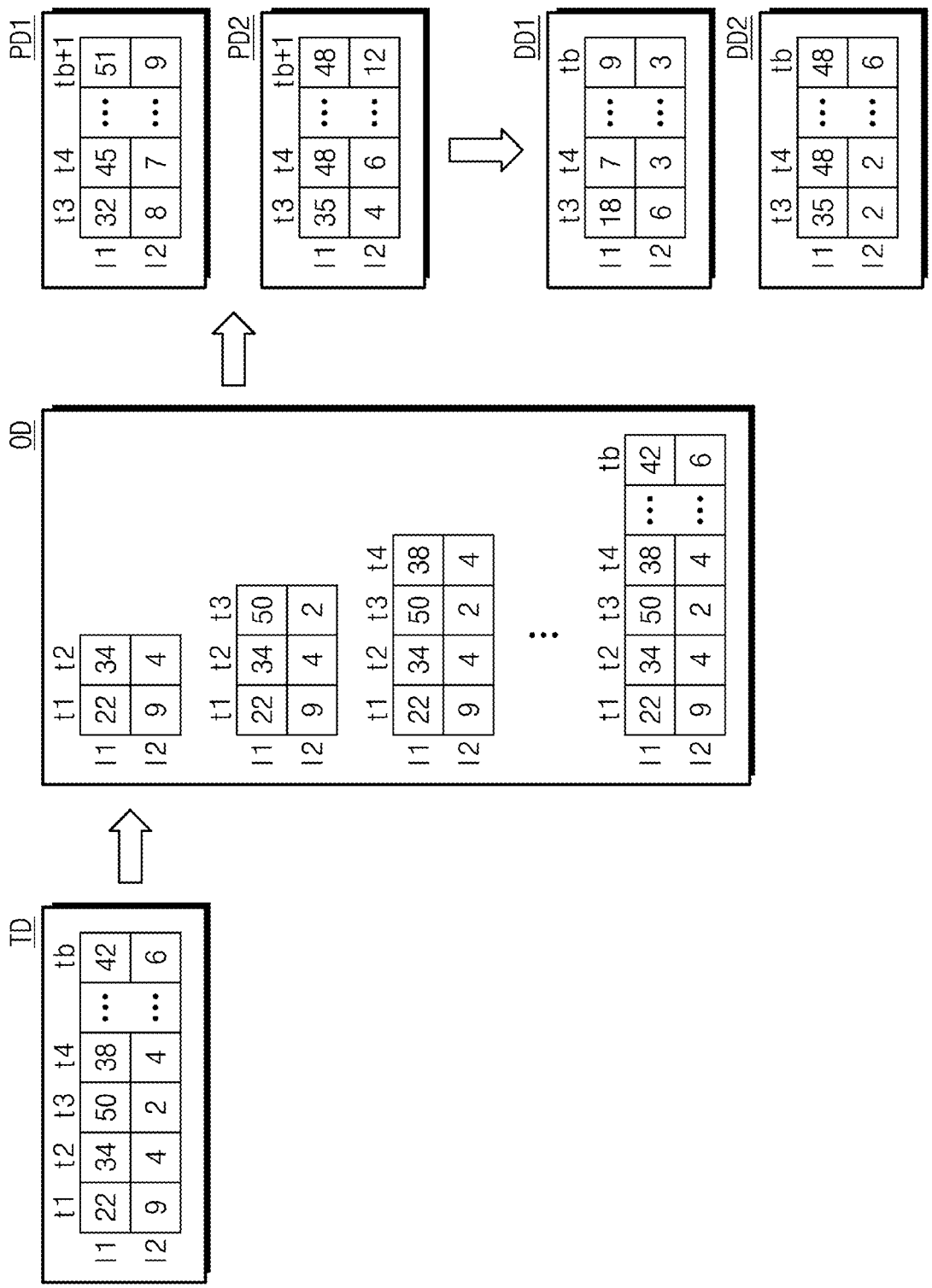
FIG. 4 is a diagram for describing time-series data, output data, device prediction results, and device errors, which are described in the data manager of FIG. 3.

FIG. 4 is a diagram for describing time-series data, output data, device prediction results, and device errors, which are described in the data manager of FIG. 3. The time-series data TD, the output data OD, device prediction results PD1 and PD2, and device errors DD1 and DD2 correspond to the time-series data TD, the output data OD, and the device prediction results PD, and the device errors DD in FIG. 3. For convenience of description, it is assumed that the device prediction results PD1 and PD2 for two prediction devices are provided to the data manager 310.

The time-series data TD includes features corresponding to each of a plurality of times t1, t2, t3, t4, . . . , tb for each of a plurality of items I1 and I2. For example, the item may indicate various health indicators such as blood pressure, blood sugar, cholesterol level, weight, or the like. The features may indicate the values of each of the items diagnosed, tested, or prescribed at a specific time.

The output data OD may be generated by accumulating features of times before each of the plurality of times t1 to tb. The output data OD may be generated from the data manager 310 or the output data generator 311 of FIG. 3. For example, the output data generator 311 may generate first cumulative data by accumulating features of times before the third time t3, may generate second cumulative data by accumulating features of times before the fourth time t4, and may generate (b−1)-th cumulative data by accumulating features of times before the (b+1)-th time 'tb+1'. The output data OD may include the first to (b−1)-th cumulative data. The prediction devices may generate prediction features corresponding to the third to (b+1)-th time t3 to 'tb+1' by analyzing each of the first to (b−1)-th cumulative data. That is, the data manager 310 may generate various cumulative data, using the time-series data TD, and thus allows the prediction devices to generate prediction results for various times.

The first device prediction result PD1 may be generated from the first prediction device 101 of FIG. 3 based on the output data OD. The second device prediction result PD2 may be generated from the second prediction device 102 of FIG. 3 based on the output data OD. Each of the first and second prediction devices 101 and 102 may generate prediction features corresponding to the third time t3 by analyzing the first cumulative data, may generate prediction features corresponding to the fourth time t4 by analyzing the second cumulative data, and may generate prediction features corresponding to the (b+1)-th time 'tb+1' by analyzing the (b−1)-th cumulative data. The first and second device prediction results PD1 and PD2 may be provided to the data manager 310 or the error calculator 312 of FIG. 3.

The first device error DD1 may be generated based on a difference between the first device prediction result PD1 and the time-series data TD. The second device error DD2 may be generated based on a difference between the second device prediction result PD2 and the time-series data TD. The error calculator 312 may calculate the difference between the prediction features of the first and second device prediction results PD1 and PD2 corresponding to the third to b-th times t3 to tb and features of the time-series data TD corresponding to the third to b-th times t3 to tb. The first and second device errors DD1 and DD2 include such the difference values. For example, 18 (i.e., a difference between 32 (the prediction feature of the first item I1 at the third time t3 of the first device prediction result PD1) and 50 (the feature of the first item I1 at the third time t3 of the time-series data TD)) may be determined as the value of the first item I1 of the first device error DD1 at the third time t3.

Figure 5:
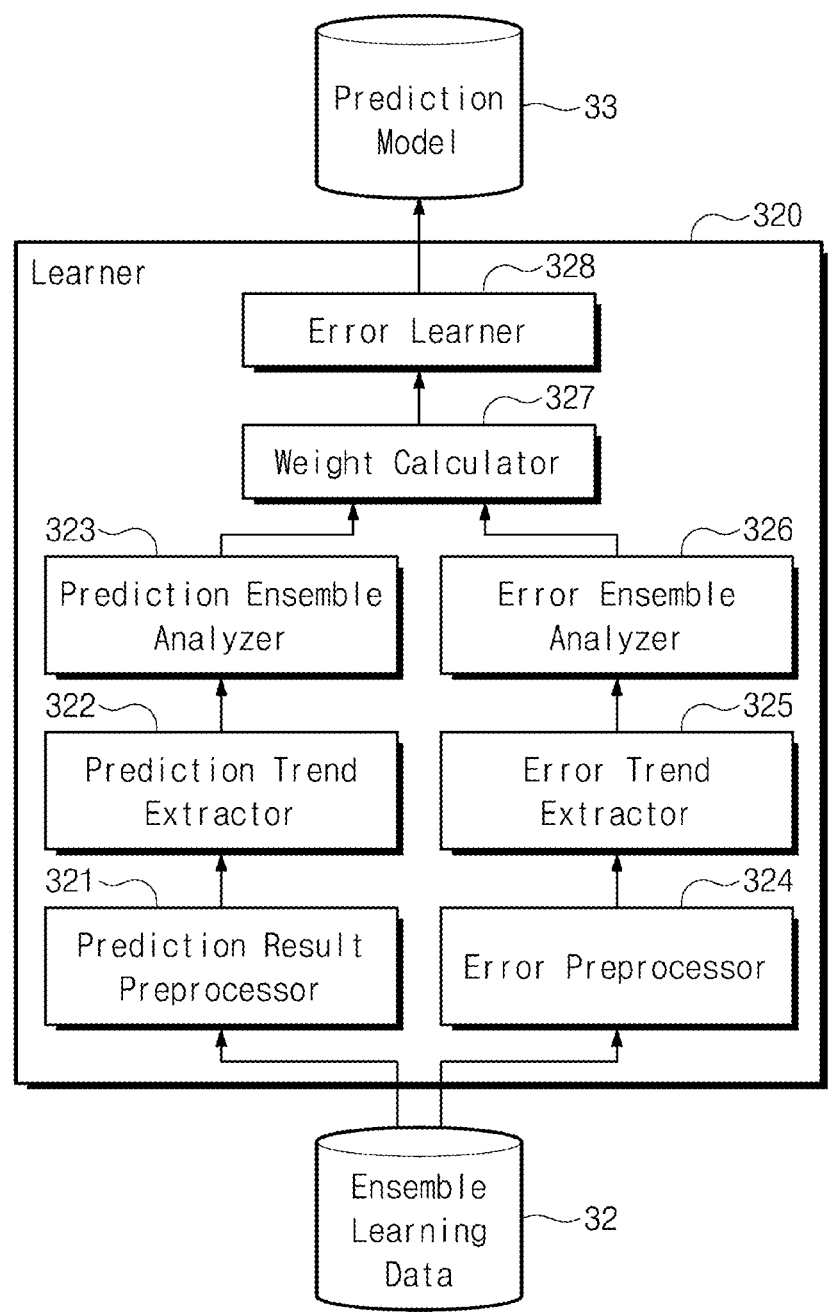
FIG. 5 is a block diagram of the learner of FIG. 2.

FIG. 5 is a block diagram of the learner of FIG. 2. It will be understood that the learner 320 of FIG. 5 is a configuration for learning the prediction model 33 and determining a parameter group based on the device prediction results and device errors described in FIG. 4. Referring to FIG. 5, the learner 320 may include a prediction result preprocessor 321, a prediction trend extractor 322, a prediction ensemble analyzer 323, an error preprocessor 324, an error trend extractor 325, an error ensemble analyzer 326, a weight calculator 327, and an error learner 328. As described above, each of the configurations included in the learner 320 may be implemented as hardware, firmware, software, or the combination thereof.

The prediction result preprocessor 321 may generate feature windows by grouping device prediction results at window time intervals. The prediction result preprocessor 321 may generate the feature windows by extracting prediction features from the device prediction results during a window time interval from a target time. Herein, the target time may be one of the third to (b+1) times t3 to 'tb+1' of FIG. 4. The feature window may include a plurality of window groups corresponding to each of the plurality of target times. For example, a window group having the window time interval of 3 and the target time of the fifth time t5 may include prediction features corresponding to the third to fifth times t3 to t5. The detailed operation of the prediction result preprocessor 321 will be described later in FIG. 6.

The prediction trend extractor 322 may generate prediction result trends by analyzing each of the plurality of window groups generated by the prediction result preprocessor 321. The prediction trend extractor 322 may generate the prediction result trends by analyzing the trend at a window time interval for the feature window. For example, the prediction trend extractor 322 may generate a trend score for each of kernel by inputting the window groups into a plurality of trend kernel functions. Such the trend score is included in the prediction result trend. The kernels may be composed of a set of parameters of an artificial neural network, and may be implemented with a convolutional layer. The detailed operation of the prediction trend extractor 322 will be described later with reference to FIG. 7.

The prediction ensemble analyzer 323 may analyze prediction result trends for each of a plurality of times to extract a prediction feature vector corresponding to a prediction time (e.g., the (b+1)-th time 'tb+1'). It will be understood that such the prediction feature vector is a feature vector for calculating device weights at the prediction time. For example, the device weight may include a first device weight corresponding to the first prediction device 101 and a second device weight corresponding to the second prediction device 102. For example, the prediction ensemble analyzer 323 may be implemented with a long short term memory (LSTM) neural network, and may sequentially input prediction result trends corresponding to each of the third to (b+1)-th times t3 to 'tb+1' into the LSTM neural network. As a result, the feature vector at the previous time may be reflected to generate the feature vector at the next time. The detailed operation of the prediction ensemble analyzer 323 will be described later with reference to FIG. 8.

The error preprocessor 324 may generate error windows by grouping device errors into window time intervals. The process of generating error windows by the error preprocessor 324 may be substantially the same as the process of generating feature windows by the prediction result preprocessor 321.

The error trend extractor 325 may generate error trends by analyzing the window groups of each of the error windows generated by the error preprocessor 324. The process of generating error trends by the error trend extractor 325 may be substantially the same as the process of generating prediction result trends by the prediction trend extractor 322.

The error ensemble analyzer 326 may analyze error trends for each of a plurality of times to extract an error feature vector corresponding to a prediction time (e.g., the (b+1)-th time 'tb+1'). The process of generating the error feature vector by the error ensemble analyzer 326 may be substantially the same as the process of generating the prediction feature vector by the prediction ensemble analyzer 323.

The weight calculator 327 may generate device weights for each of a plurality of prediction devices based on the prediction feature vector and the error feature vector. The weight calculator 327 may analyze the prediction feature vector and the error feature vector in units of items, and may fuse the analysis result of the prediction feature vector and the analysis result of the error feature vector for each of the items. Accordingly, the weight calculator 327 may generate device weights for each of the items. The detailed operation of the weight calculator 327 will be described later with reference to FIG. 9.

The error learner 328 may compare the device weights generated from the weight calculator 327 with a reference device weight, and then may adjust a parameter group for the operation of each configuration illustrated in FIG. 5 by using a backpropagation scheme. Here, the reference device weight may be generated by calculating a difference between prediction features of a prediction time of each of the device prediction results and the actually-measured value at the prediction time. For example, the prediction device having a minimum difference in each of the items and the remaining prediction devices may be distinguished by different values in the reference device weight. The error learner 328 may calculate the error of device weights by calculating the sum of the square root of the difference between the reference device weight and a device weight. The error learner 328 may adjust the parameter group by using the backpropagation scheme such that the size of the error is minimized. The detailed operation of the error learner 328 will be described later with reference to FIG. 10.

Figure 6:
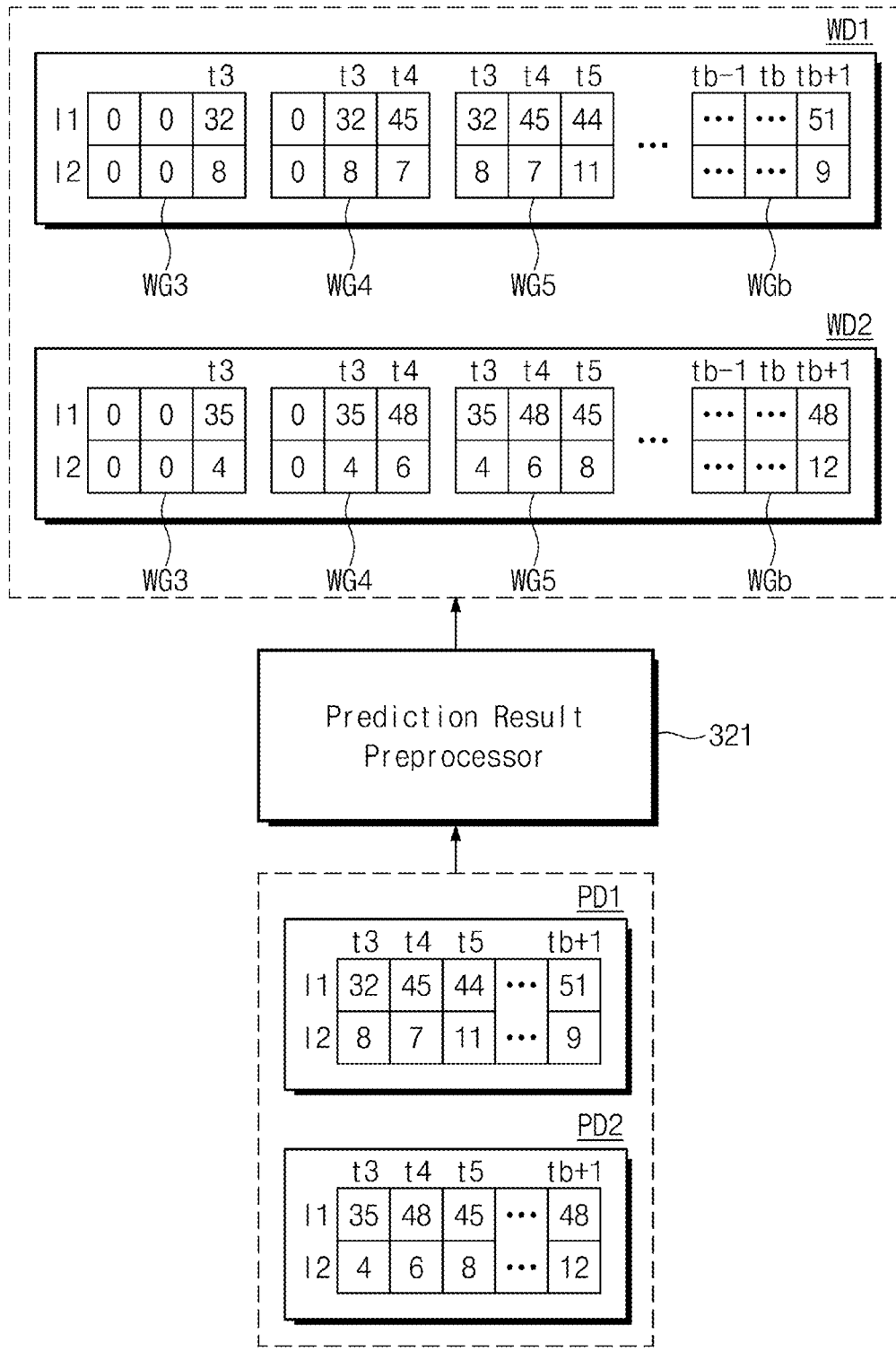
FIG. 6 is a diagram for describing an operation of the prediction result preprocessor of FIG. 5.

FIG. 6 is a diagram for describing an operation of the prediction result preprocessor of FIG. 5. Except that the entered data is different, the operation of the error preprocessor 324 of FIG. 5 is substantially the same as the operation of the prediction result preprocessor 321. Referring to FIG. 6, the first device prediction result PD1 and the second device prediction result PD2 are input into the prediction result preprocessor 321. The first device prediction result PD1 and the second device prediction result PD2 include prediction features corresponding to each of the first and second items I1 and I2 at the third to (b+1)-th time t3 to 'tb+1'.

The prediction result preprocessor 321 may group first and second device prediction results PD1 and PD2 into window time intervals to generate the first and second feature windows WD1 and WD2. For example, it is assumed that the window time interval of FIG. 6 is 3. The prediction result preprocessor 321 may extract prediction features corresponding to three times to generate window groups WG3, WG4, WG5, . . . , WGb of each of first and second feature windows WD1 and WD2. Each of the window groups WG3 to WGb may include prediction features during three consecutive times. The window groups WG3 to WGb may be used to analyze the trend of prediction features during the window time interval.

There are no prediction features for the previous times of the third time t3 in the first and second device prediction results PD1 and PD2. Accordingly, the values (e.g., the first and second times t1 and t2 of FIG. 4) of the time at which the window groups WG3 and WG4 generated based on the third time t3 or the fourth time t4 are empty may be filled through zero-padding.

Figure 7:
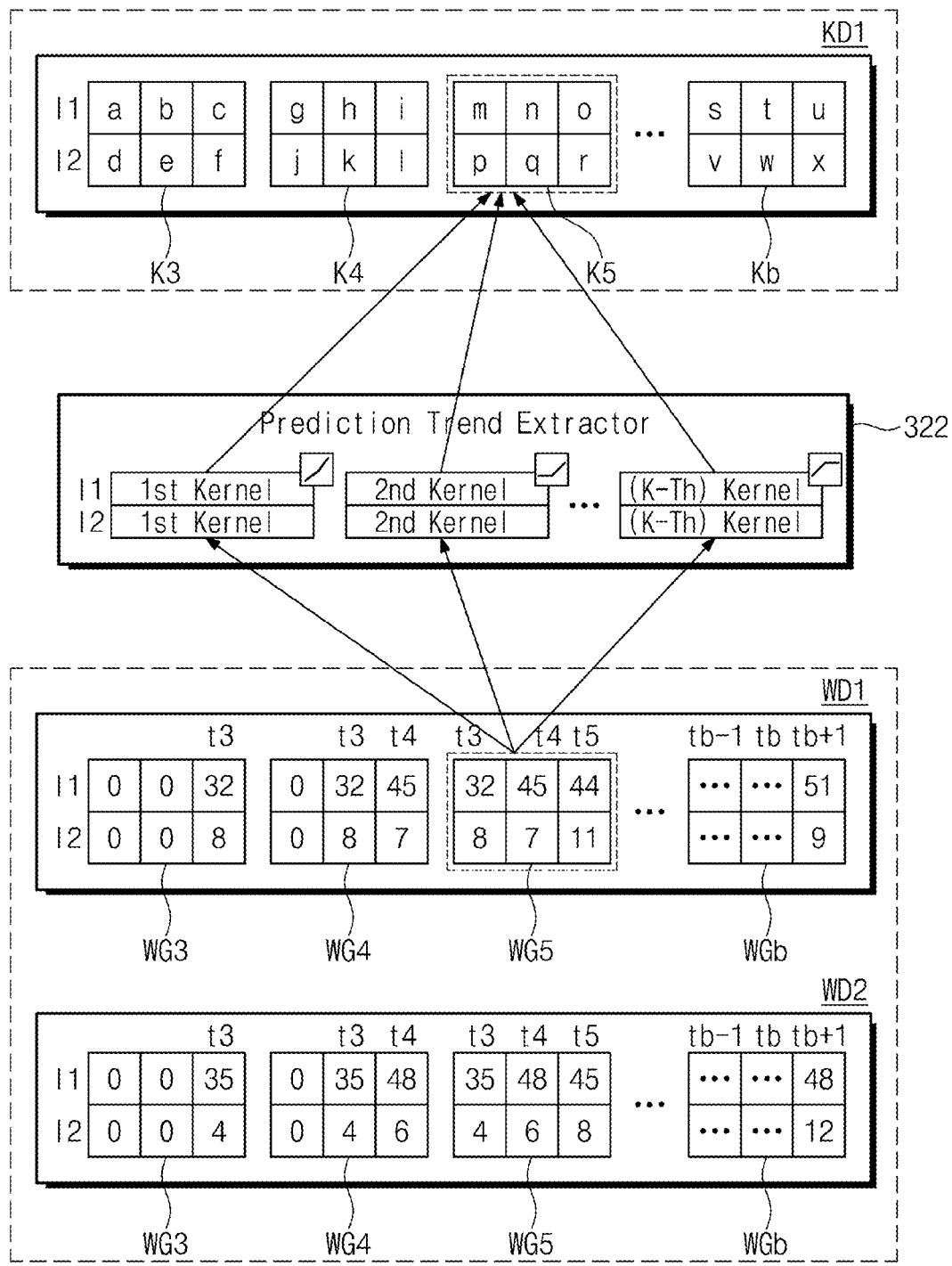
FIG. 7 is a diagram for describing an operation of the prediction trend extractor of FIG. 5.

FIG. 7 is a diagram for describing an operation of the prediction trend extractor of FIG. 5. Except that the entered data is different, the operation of the error trend extractor 325 of FIG. 5 is substantially the same as the operation of the prediction trend extractor 322. Referring to FIG. 7, the first and second feature windows WD1 and WD2 generated by the prediction result preprocessor 321 of FIG. 6 are input into the prediction trend extractor 322. The first and second feature windows WD1 and WD2 include prediction features during a window time interval.

The prediction trend extractor 322 may generate a prediction result trend KD1 by analyzing each of the window groups WG3 to WGb. The prediction result trend KD1 may include trend features K3 to Kb corresponding to each of the window groups WG3 to WGb. The prediction trend extractor 322 may generate the prediction result trend KD1 by analyzing the trend of prediction features in a window time interval. For example, each of the window groups WG3 to WGb may be input into a plurality of trend kernel functions (the first to k-th kernels). For example, each of the first to k-th kernels may be a trend kernel function for analyzing a tendency to maintain predictions, a tendency to increase predictions, and a tendency to decrease predictions.

The prediction trend extractor 322 may generate trend scores corresponding to each of the first to k-th kernels. The trend scores are included in the trend features K3 to Kb. For example, in the case of the first item I1, the trend score generated by inputting the window group WG5 into the first kernel may be 'm'; in the case of the second item I2, the trend score may be 'p'. In the case of the first item I1, the trend score generated by inputting the window group WG5 into the second kernel may be 'n'; in the case of the second item I2, the trend score may be 'q'. For example, the number of trend scores corresponding to a single window group may depend on the number of kernels and the number of items.

The kernels may be composed of a set of parameters of an artificial neural network, and may be implemented with a convolutional layer. For example, when there is one item in the first and second feature windows WD1 and WD2, the trend score may be calculated through one-dimensional convolution. For example, when there are a plurality of items in the first and second feature windows WD1 and WD2, the trend score in which the correlation between items is considered may be calculated through two-dimensional convolution. The parameters of each of the kernels may be learned and adjusted by using the backpropagation scheme described in FIG. 5.

Figure 8:
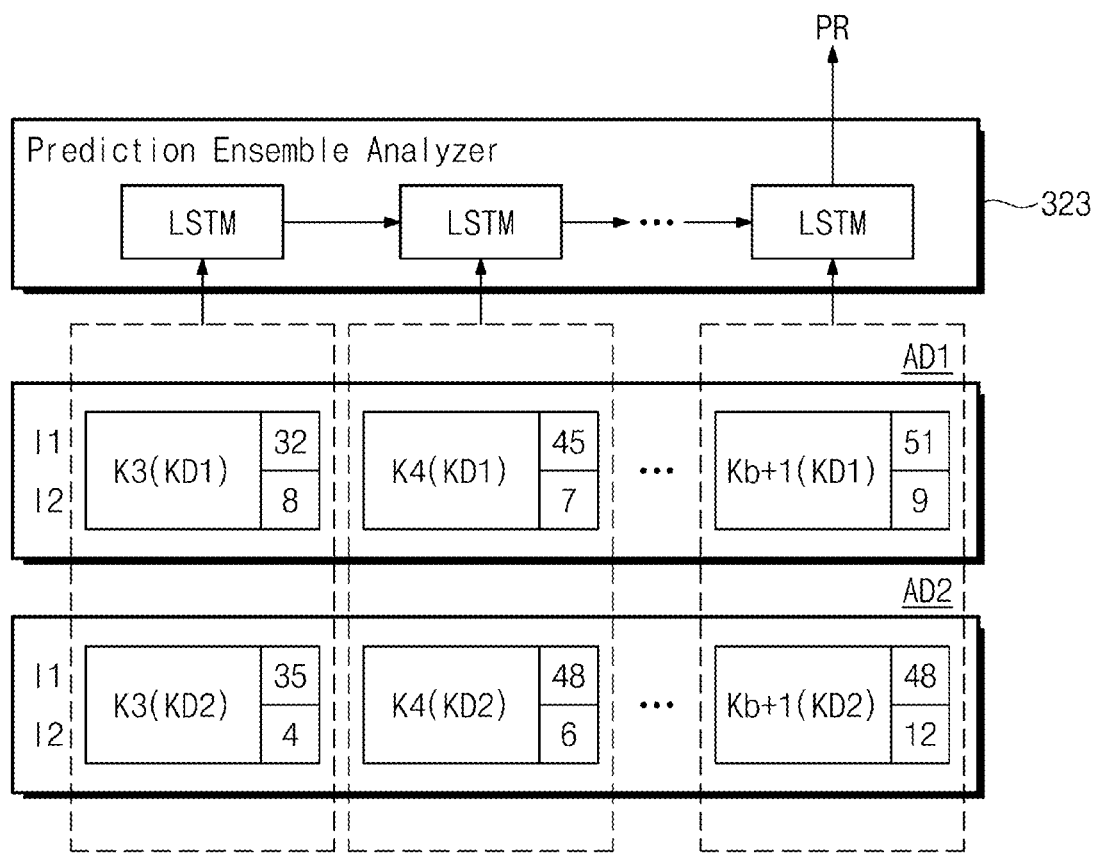
FIG. 8 is a diagram for describing an operation of the prediction ensemble analyzer of FIG. 5.

FIG. 8 is a diagram for describing an operation of the prediction ensemble analyzer of FIG. 5. Except that the entered data is different, the operation of the error ensemble analyzer 326 of FIG. 5 is substantially the same as the operation of the prediction ensemble analyzer 323. Referring to FIG. 8, the prediction result trends KD1 and KD2 and the device prediction results PD1 and PD2, which are generated by the prediction trend extractor 322 of FIG. 7, are combined and input into the prediction ensemble analyzer 323.

The prediction ensemble analyzer 323 receives the prediction result trends KD1 and KD2 and the device prediction results PD1 and PD2. Each of the prediction result trends KD1 and KD2 includes trend features K3 to Kb. The prediction ensemble analyzer 323 may generate analysis data AD1 and AD2 by combining the device prediction results PD1 and PD2 of a target time corresponding to each of the trend features K3 to Kb. For example, the trend features K3 and the device prediction results PD1 and PD2 (32, 8, 35, or 4 that is a device prediction result value corresponding to the third time t3 in FIG. 4), which correspond to the third time t3, may be combined with each other.

The prediction ensemble analyzer 323 may sequentially input analysis data AD1 and AD2 corresponding to each of the third to (b+1)-th times t3 to 'tb+1' to an LSTM neural network. For example, the analysis data AD1 and AD2 corresponding to the third time t3 may be input to the LSTM neural network, and the feature vector corresponding to the third time t3 may be generated. Afterward, the analysis data AD1 and AD2 corresponding to the fourth time t4 may be input to the LSTM neural network; the feature vector corresponding to the third time t3 may be reflected; a feature vector corresponding to the fourth time t4 may be generated. A prediction feature vector PR corresponding to the (b+1)-th time 'tb+1' may be generated by repeating this process. The (b+1)-th time may be a prediction time. It will be understood that the prediction feature vector PR is a feature vector for calculating device weights (first and second device weights) at a prediction time. The parameters of the LSTM neural network may be learned and adjusted by using the backpropagation scheme described in FIG. 5.

Figure 9:
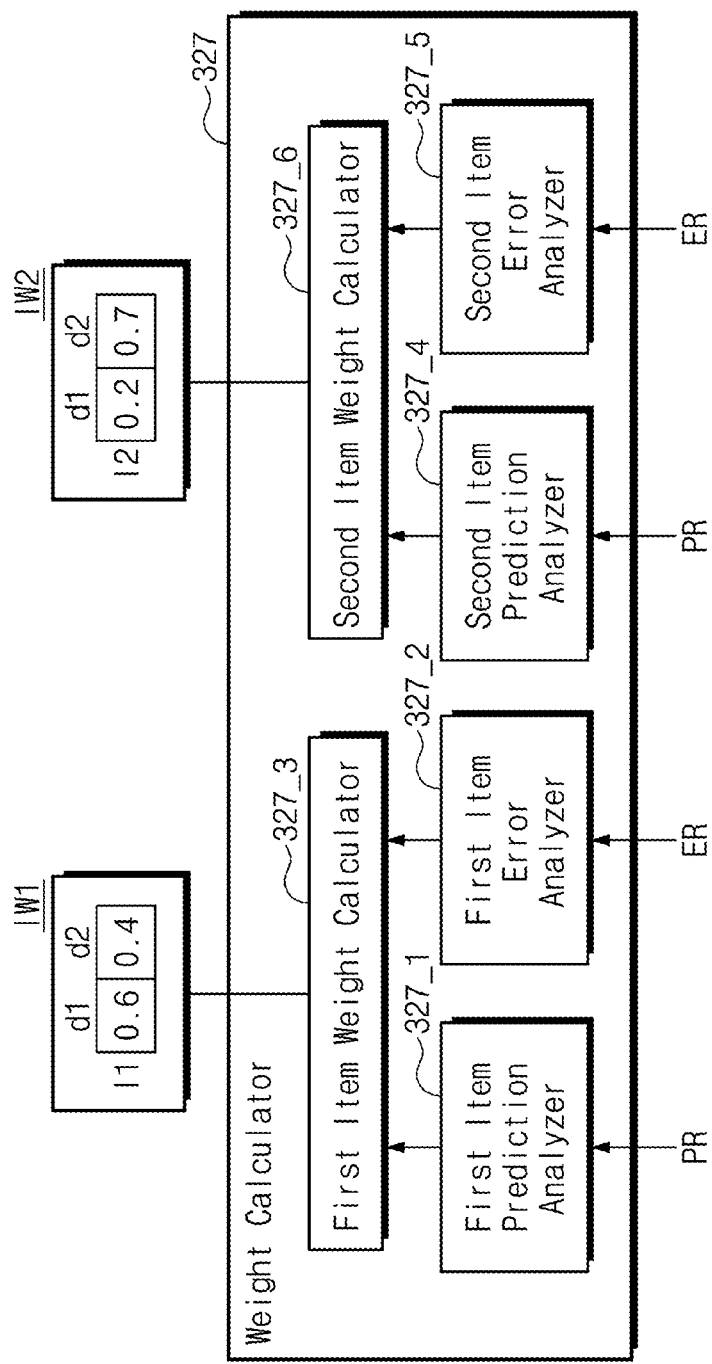
FIG. 9 is a diagram for describing an operation of the weight calculator of FIG. 5.

FIG. 9 is a diagram for describing an operation of the weight calculator of FIG. 5. Referring to FIG. 9, the weight calculator 327 may include a first item prediction analyzer 327_1, a first item error analyzer 327_2, a first item weight calculator 327_3, a second item prediction analyzer 327_4, a second item error analyzer 327_5, and a second item weight calculator 327_6.

The first item prediction analyzer 327_1 may extract a feature corresponding to the first item I1 from a prediction feature vector PR. The first item error analyzer 327_2 may extract a feature corresponding to the first item I1 from a prediction error vector ER. Herein, the prediction feature vector PR corresponds to the prediction feature vector PR described in FIG. 8. Herein, it will be understood that the prediction error vector ER is an error vector corresponding to the prediction time generated by performing the processes of FIGS. 6 to 8 in the error preprocessor 324, the error trend extractor 325, and the error ensemble analyzer 326 of FIG. 5.

The first item weight calculator 327_3 may generate device weights IW1 corresponding to the first item I1, by fusing the features extracted from the first item prediction analyzer 327_1, and the features extracted from the first item error analyzer 327_2. For example, the device weights IW1 corresponding to the first item I1 may include a weight value corresponding to the first prediction device d1 and a weight value corresponding to the second prediction device d2.

The second item prediction analyzer 327_4 may extract a feature corresponding to the second item I2 from the prediction feature vector PR. The second item error analyzer 327_5 may extract a feature corresponding to the second item I2 from the prediction error vector ER. The second item weight calculator 327_6 may generate device weights IW2 corresponding to the second item I2, by fusing the features extracted from the second item prediction analyzer 327_4 and the features extracted from the second item error analyzer 327_5. For example, the device weights IW2 corresponding to the second item I2 may include a weight value corresponding to the first prediction device d1 and a weight value corresponding to the second prediction device d2.

Figure 10:
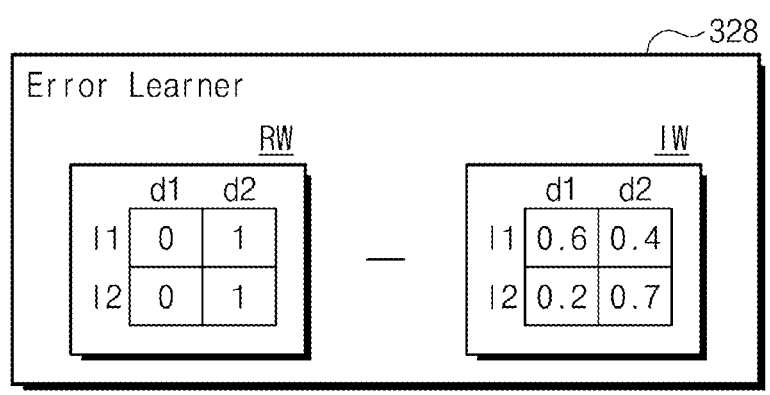
FIG. 10 is a diagram for describing an operation of the error learner of FIG. 5.

FIG. 10 is a diagram for describing an operation of the error learner of FIG. 5. The error learner 328 may receive a device weight IW in which the device weights IW1 and IW2 generated from the weight calculator 327 of FIG. 9 are merged with each other. The error learner 328 may generate a reference device weight RW for error learning.

The reference device weight RW may be generated by calculating a difference between prediction features at each prediction time in each of the device prediction results and the actually-measured value at the prediction time. For example, the difference between the first device prediction result corresponding to the prediction time and the actually-measured value at a preset prediction time may be calculated. In addition, the difference between the second device prediction result corresponding to the prediction time and the actually-measured value at a preset prediction time may be calculated. The weight value for the prediction device (e.g., the second prediction device), which has the smallest difference, from among prediction devices d1 and d2 may be set to 1; the weight value for the remaining prediction device (e.g., the first prediction device) may be set to 0. The weight value may be set for each of the items I1 and I2. As a result, the reference device weight RW may be generated.

The error learner 328 may calculate the difference in the device weight IW calculated from the reference device weight RW for each of the items I1 and I2 and for each of the devices d1 and d2. The error learner 328 may calculate the square root of the difference and may add the calculated values (a total of four calculated values in the case of FIG. 10). The parameter group may be adjusted such that the summed values are minimized. The error learner 328 may adjust a parameter group for the operation of each component illustrated in FIG. 5 in the above-described backpropagation scheme.

Figure 11:
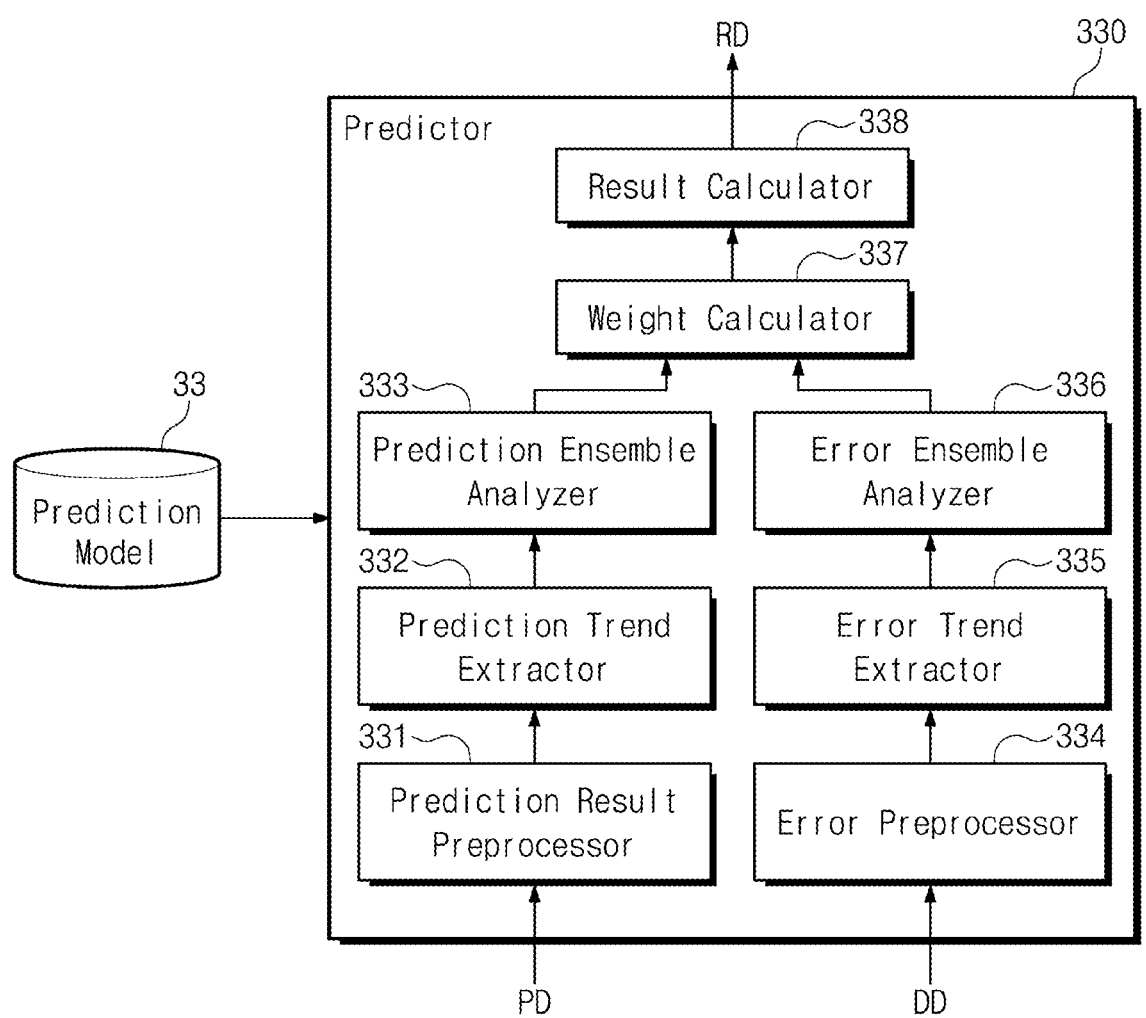
FIG. 11 is a block diagram of the predictor of FIG. 2.

FIG. 11 is a block diagram of the predictor of FIG. 2. It will be understood that the predictor 330 of FIG. 11 is a configuration for generating the ensemble result of prediction results received from a plurality of prediction devices based on the learned prediction model 33 and a parameter group. Referring to FIG. 11, the predictor 330 may include a prediction result preprocessor 331, a prediction trend extractor 332, a prediction ensemble analyzer 333, an error preprocessor 334, an error trend extractor 335, an error ensemble analyzer 336, a weight calculator 337, and a result calculator 338. As described above, each of the configurations included in the predictor 330 may be implemented as hardware, firmware, software, or the combination thereof.

The predictor 330 analyzes the device prediction results PD and the device errors DD and generates the ensemble result RD, based on the learned prediction model 33. The prediction result preprocessor 331, the prediction trend extractor 332, the prediction ensemble analyzer 333, the error preprocessor 334, the error trend extractor 335, the error ensemble analyzer 336, and the weight calculator 337 may perform substantially the same operation as the prediction result preprocessor 321, the prediction trend extractor 322, the prediction ensemble analyzer 323, the error preprocessor 324, the error trend extractor 325, the error ensemble analyzer 326, and the weight calculator 327, which are described in FIGS. 5 to 9.

The result calculator 338 may generate the final ensemble result RD by applying the device weights generated from the weight calculator 337 to the device prediction results.

Figure 12:
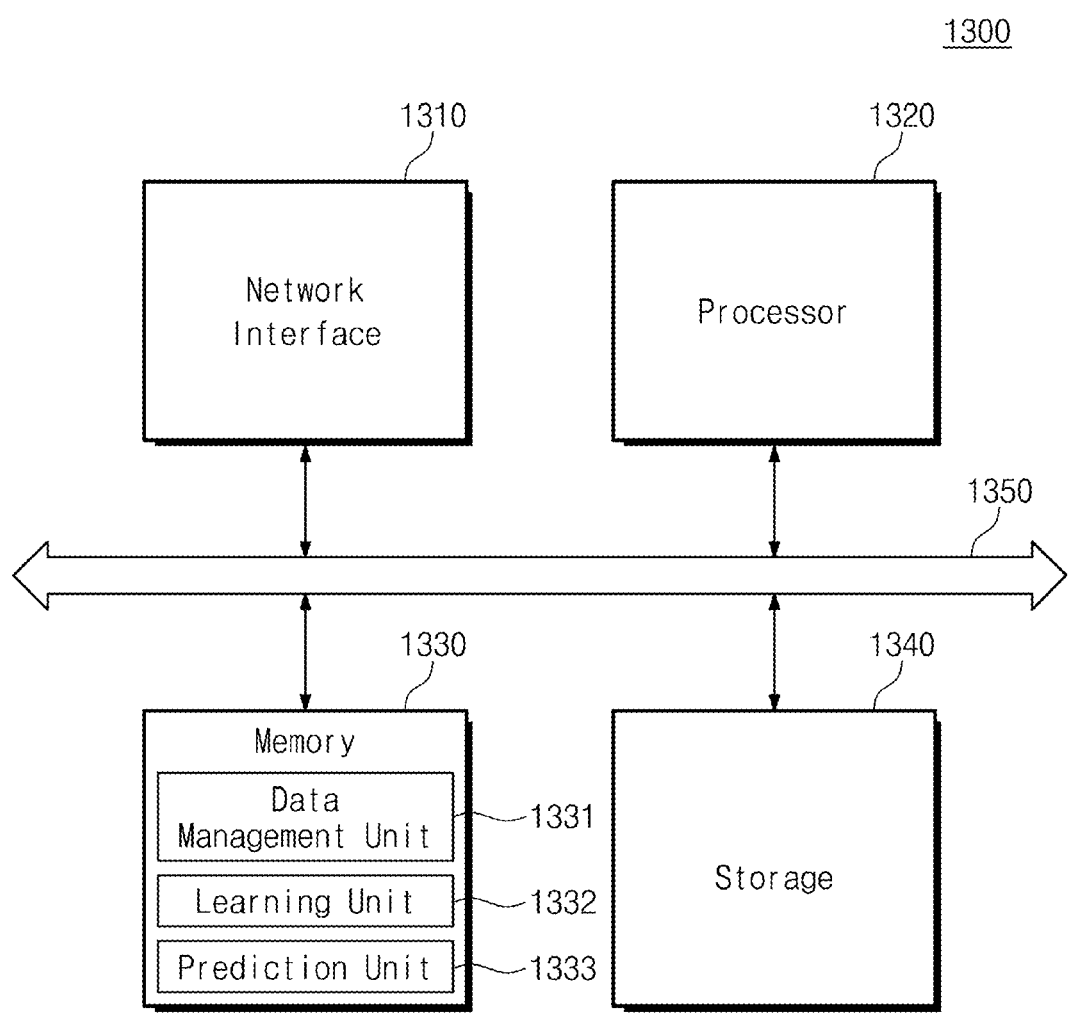
FIG. 12 is a block diagram of the ensemble prediction device of FIG. 1.

FIG. 12 is a block diagram of the ensemble prediction device of FIG. 1. Referring to FIG. 12, an ensemble prediction device 1300 may include a network interface 1310, a processor 1320, a memory 1330, storage 1340, and a bus 1350. For example, the ensemble prediction device 1300 may be implemented as a server, but is not limited thereto.

The network interface 1310 is configured to communicate with the terminal 200 or the first to n-th prediction devices 101 to 10n through the network 400 of FIG. 1. The network interface 1310 may provide data, which is received through the network 400, to the processor 1320, the memory 1330, or the storage 1340 through the bus 1350. The network interface 1310 may output the output data to the first to n-th prediction devices 101 to 10n together with a prediction request by the processor 1320. Besides, the network interface 1310 may receive device prediction results generated in response to the output data.

The processor 1320 may function as the central processing device of the ensemble prediction device 1300. The processor 1320 may perform a control operation and a calculation operation required for the data management, data learning, and data prediction of the ensemble prediction device 1300. For example, under the control of the processor 1320, the network interface 1310 may transmit the output data to the first to n-th prediction devices 101 to 10n, and may receive the device prediction results from the first to n-th prediction devices 101 to 10n. Under the control of the processor 1320, the weight group of a prediction model may be adjusted, and an ensemble result may be calculated using the prediction model. The processor 1320 may operate by utilizing the computational space of the memory 1330 and may read files for driving an operating system and execution files of an application from the storage 1340. The processor 1320 may execute an operating system and various applications.

The memory 1330 may store data and process codes, which are processed or scheduled to be processed by the processor 1320. For example, the memory 1330 may include the device prediction results, pieces of information for managing the device prediction results, pieces of information for generating a weight group, pieces of information for calculating an ensemble result, and pieces of information for building a prediction model. The memory 1330 may be used as a main memory device of the ensemble prediction device 1300. The memory 1330 may include a dynamic random access memory (DRAM), a static RAM (SRAM), a phase-change RAM (PRAM), a magnetic RAM (MRAM), a ferroelectric RAM (FeRAM), a resistive RAM (RRAM), etc.

A data management unit 1331, a learning unit 1332, and a prediction unit 1333 may be loaded and executed onto the memory 1330. The data management unit 1331, the learning unit 1332, and the prediction unit 1333 correspond to the data manager 310, the learner 320, and the predictor 330 of FIG. 2, respectively. The data management unit 1331, the learning unit 1332, and the prediction unit 1333 may be the part of the computational space of the memory 1330. In this case, the data management unit 1331, the learning unit 1332, and the prediction unit 1333 may be implemented with firmware or software. For example, the firmware may be stored in the storage 1340 and then may be loaded onto the memory 1330 when the firmware is executed. The processor 1320 may execute the firmware loaded onto the memory 1330.

The data management unit 1331 may load time-series data included in raw learning data stored in the storage 1340 and may generate output data, under the control of the processor 1320. The data management unit 1331 may be operated to transmit the output data to the first to n-th prediction devices 101 to 10n through the network interface 1310. The data management unit 1331 may generate device errors by calculating the difference between time-series data and device prediction results. Under the control of the processor 1320, the learning unit 1332 may be operated to generate and adjust a weight group by analyzing the device prediction results and the device errors. The prediction unit 1333 may be operated to generate the ensemble result based on the prediction model under the control of the processor 1320.

The storage 1340 may store data generated for long-term storage by an operating system or applications, a file for operating an operating system, the execution files of applications, or the like. For example, the storage 1340 may store files for executing the data management unit 1331, the learning unit 1332, and the prediction unit 1333. The storage 1340 may be used as an auxiliary memory device of the ensemble prediction device 1300. The storage 1340 may include a flash memory, a PRAM, an MRAM, a FRAM, an RRAM, etc.

The bus 1350 may provide a communication path between the components of the ensemble prediction device 1300. The network interface 1310, the processor 1320, the memory 1330, and the storage 1340 may exchange data with each other through the bus 1350. The bus 1350 may be configured to support various types of communication formats used in the ensemble prediction device 1300.

The above-mentioned description refers to embodiments for implementing the scope of the present disclosure. Embodiments in which a design is changed simply or which are easily changed may be included in the scope of the present disclosure as well as an embodiment described above. In addition, technologies that are easily changed and implemented by using the above-mentioned embodiments may be also included in the scope of the present disclosure.

According to an embodiment of the present disclosure, the accuracy and reliability of the ensemble result of prediction results for each device may be improved by building a prediction model to consider prediction results, errors, and trends for each device.

Furthermore, according to an embodiment of the present disclosure, the learning efficiency of the prediction model may be improved by generating output data such that the prediction models for each device generate prediction results for each time.

While the present disclosure has been described with reference to embodiments thereof, it will be apparent to those of ordinary skill in the art that various changes and modifications may be made thereto without departing from the spirit and scope of the present disclosure as set forth in the following claims.

What is claimed is:

1. A device which ensembles data received from a plurality of prediction devices through a wireless or wired network, the device comprising:
    a data manager configured to generate output data based on time-series data, to provide the output data to a first prediction device and a second prediction device through the network, to receive a first device prediction result corresponding to the output data from the first prediction device through the network, to receive a second device prediction result corresponding to the output data from the second prediction device through the network, to calculate a first device error based on a difference between the first device prediction result and the time-series data, and to calculate a second device error based on a difference between the second device prediction result and the time-series data;
    a learner configured to adjust a parameter group of a prediction model for generating a first device weight corresponding to the first prediction device and a second device weight corresponding to the second prediction device, based on the first device prediction result, the second device prediction result, the first device error, and the second device error; and
    a predictor configured to apply the first device weight to the first device prediction result to generate a first result, apply the second device weight to the second device prediction result to generate a second result, and to generate an ensemble result based on the first result and the second result,
    wherein the ensemble result is provided to a terminal,
    wherein the time-series data includes a plurality of features of an item at a plurality of times, respectively, the plurality of times being from a first time to a N-th time,
    wherein the data manger generates the output data by sequentially generating (N−1) cumulative data, each subsequent pair of the (N−1) cumulative data including first cumulative data and second cumulative data, the first cumulative data including a first plurality of features of the item in the time-series data at a first plurality of times from the first time to an i-th time to generate prediction features of the first and second device prediction results corresponding to an (i+1)-th time, the second cumulative data including a second plurality of features of the item in the time-series data at a second plurality of times from the first time to a (i+1)-th time to generate prediction features of the first and second device prediction results corresponding to an (i+2)-th time.

2. The device of claim 1, wherein the first prediction device generates first prediction features corresponding to the second time based on the first cumulative data, generates second prediction features corresponding to a third time after the second time based on the second cumulative data, and generates the first device prediction result including the first prediction features and the second prediction features, and
    wherein the second prediction device generates third prediction features corresponding to the second time based on the first cumulative data, generates fourth prediction features corresponding to the third time after the second time based on the second cumulative data, and generates the second device prediction result including the third prediction features and the fourth prediction features.

3. The device of claim 1, wherein the learner extracts prediction features during a window time interval before a target time from the first device prediction result to generate a first feature window, extracts prediction features during the window time interval before the target time from the second device prediction result to generate a second feature window, extracts prediction features during the window time interval before the target time from the first device error to generate a first error window, extracts prediction features during the window time interval before the target time from the second device error to generate a second error window, and adjusts the parameter group based on the first feature window, the second feature window, the first error window, and the second error window.

4. The device of claim 3, wherein the learner generates the first and second feature windows and the first and second error windows by making zero-padding on values for a time before the target time when the target time is a first time of the first and second device prediction results and the first and second device errors.

5. The device of claim 3, wherein the learner analyzes a trend of the window time interval for the first feature window to generate a first prediction result trend, analyzes a trend of the window time interval for the second feature window to generate a second prediction result trend, analyzes a trend of the window time interval for the first error window to generate a first error trend, analyzes a trend of the window time interval for the second error window to generate a second error trend, and adjusts the parameter group based on the first prediction result trend, the second prediction result trend, the first error trend, and the second error trend.

6. The device of claim 5, wherein the learner extracts a prediction feature vector corresponding to a prediction time based on the first and second prediction result trends and the first and second device prediction results, and extracts a prediction error vector corresponding to the prediction time based on the first and second error trends and the first and second device errors.

7. The device of claim 6, wherein the learner generates the first device weight and the second device weight, based on the prediction feature vector and the prediction error vector, and
wherein each of the first device weight and the second device weight includes weight values corresponding to each of a plurality of items.

8. The device of claim 5, wherein the learner generates first analysis data by combining features of the first device prediction result at a third plurality of times from a third time to a (N+1)-th time and features of the first prediction result trend at the third plurality of times, respectively, generates second analysis data by combining features of the second device prediction result at the third plurality of times and features of the second prediction result trend at the third plurality of times, respectively, extracts a prediction feature vector corresponding to a prediction time based on the first and second analysis data, and extracts a prediction error vector corresponding to the prediction time based on the first and second error trends and the first and second device errors.

9. The device of claim 8, wherein the learner sequentially inputs the first and second analysis data to a long short term memory (LSTM) neural network to generate the prediction feature vector.

10. The device of claim 1, wherein the learner generates the first device weight and the second device weight based on the first device prediction result, the second device prediction result, the first device error, and the second device error, generates a reference device weight based on the first device prediction result and the second device prediction result, and compares the reference device weight with the first and second device weights to adjust the parameter group.

11. The device of claim 10, wherein the learner calculates a first difference between a prediction feature of the first device prediction result corresponding to a prediction time and an actually-measured value corresponding to the prediction time, calculates a second difference between a prediction feature of the second device prediction result corresponding to the prediction time and the actually-measured value, and generates the reference device weight based on the first difference and the second difference.

12. A device which ensembles data received from a plurality of prediction devices through a wireless or wired network, the device comprising:
a data manager configured to provide output data to a first prediction device and a second prediction device through the network, to receive a first device prediction result corresponding to the output data from the first prediction device through the network, and to receive a second device prediction result corresponding to the output data from the second prediction device through the network; and
a predictor configured to generate a prediction feature vector corresponding to a prediction time, based on the first device prediction result, the second device prediction result, a first trend of the first device prediction result during a window time interval, and a second trend of the second device prediction result during the window time interval, to generate a first device weight and a second device weight of each of a plurality of items, based on the prediction feature vector, and to generate an ensemble result of the first and second device prediction results corresponding to the prediction time, based on the first device weight and the second device weight,
wherein the data manager generates the output data based on time-series data, the time-series data including a plurality of features of an item at a plurality of times, respectively, the plurality of times being from a first time to a N-th time,
wherein the data manger generates the output data by sequentially generating (N−1) cumulative data, each subsequent pair of the (N−1) cumulative data including first cumulative data and second cumulative data, the first cumulative data including a first plurality of features of the item in the time-series data at a first plurality of times from the first time to an i-th time to generate prediction features of the first and second device prediction results corresponding to an (i+1)-th time, the second cumulative data including a second plurality of features of the item in the time-series data at a second plurality of times from the first time to a i+1)-th time to generate prediction features of the first and second device prediction results corresponding to an (1+2)-th time,
wherein the predictor applies the first device weight to the first device prediction result corresponding to the prediction time to generate a first result, applies the second device weight to the second device prediction result corresponding to the prediction time to generate a second result, and generates the ensemble result based on the first result and the second result, and the ensemble result is provided to a terminal.

13. The device of claim 12, wherein the data manager calculates a first device error based on a difference between the first device prediction result and the time-series data, and calculates a second device error based on a difference between the second device prediction result and the time-series data, and
wherein the predictor generates a prediction error vector corresponding to the prediction time, based on the first device error, the second device error, a third trend of the first device error during the window time interval, and a fourth trend of the second device prediction result during the window time interval, and generates the first device weight and the second device weight further based on the prediction error vector.

14. The device of claim 12, wherein the predictor extracts prediction features during the window time interval before a target time from the first device prediction result to generate a first feature window, extracts prediction features during the window time interval before the target time from the second device prediction result to generate a second feature window, generates the first trend based on the first feature window, and generates the second trend based on the second feature window.

15. The device of claim 14, wherein the predictor generates the first and second feature windows by making zero-padding on values a time before the target time when the target time is a first time of the first and second device prediction results.

16. The device of claim 12, wherein the predictor generates the prediction feature vector based on a feature vector generated by the first and second trends corresponding to a time before the prediction time, the first and second trends corresponding to the prediction time, and the first and second device prediction results corresponding to the prediction time.

17. An operating method of a device which ensembles data received from a plurality of prediction devices through a wireless or wired network, the method comprising:
  generating output data based on time-series data;
  transmitting the output data together with a prediction request to a first prediction device and a second prediction device through the network;
  receiving a first device prediction result obtaining by responding to the prediction request, from the first prediction device through the network;
  receiving a second device prediction result obtaining by responding to the prediction request, from the second prediction device through the network;
  calculating a first device error based on a difference between the first device prediction result and the time-series data;
  calculating a second device error based on a difference between the second device prediction result and the time-series data; and
  generating a first device weight corresponding to the first prediction device and a second device weight corresponding to the second prediction device, based on the first device prediction result, the second device prediction result, the first device error, and the second device error;
  applying the first device prediction result corresponding to a prediction time to the first device weight to generate a first result;
  applying the second device prediction result corresponding to the prediction time to the second device weight to generate a second result;
  generating an ensemble result based on the first result and the second result; and
  providing the ensemble result to a terminal,
  wherein the time-series data includes a plurality of features of an item at a plurality of times, respectively, the plurality of times being from a first time to a N-th time,
  wherein the output data is generated by sequentially generating (N−1) cumulative data, each subsequent pair of the (N−1) cumulative data including first cumulative data and second cumulative data, the first cumulative data including a first plurality of features of the item in the time-series data at a first plurality of times from the first time to an i-th time to generate prediction features of the first and second device prediction results corresponding to an (i+1)-th time, the second cumulative data including a second plurality of features of the item in the time-series data at a second plurality of times from the first time to a (i+1)-th time to generate prediction features of the first and second device prediction results corresponding to an (1+2)-th time.

18. The method of claim 17, wherein the generating of the first device weight and the second device weight includes:
  analyzing the first device prediction result during a window time interval to generate a first prediction result trend;
  analyzing the second device prediction result during the window time interval to generate a second prediction result trend;
  analyzing the first device error during the window time interval to generate a first error trend;
  analyzing the second device error during the window time interval to generate a second error trend;
  generating a feature vector corresponding to a prediction time based on the first and second prediction result trends and the first and second device prediction results;
  generating an error vector corresponding to the prediction time based on the first and second error trends and the first and second device errors; and
  generating the first and second device weights based on the feature vector and the error vector.

19. The method of claim 17, further comprising:
  comparing a reference device weight with the first device weight and the second device weight to adjust a parameter of a prediction model.

* * * * *